(12) United States Patent
Khan et al.

(10) Patent No.: US 10,893,826 B2
(45) Date of Patent: Jan. 19, 2021

(54) ELECTRONIC CALIPER FOR ASSESSING PATIENT BIOMECHANICS

(71) Applicant: KKT International Ltd., St. Michael (BB)

(72) Inventors: Aslam Khan, Mississauga (CA); Henri Corniere, Vanouver (CA)

(73) Assignee: KKT International, LTD

( * ) Notice: Subject to any disclaimer, the term of this patent is extended or adjusted under 35 U.S.C. 154(b) by 307 days.

(21) Appl. No.: 15/992,054

(22) Filed: May 29, 2018

(65) Prior Publication Data

US 2018/0317810 A1 Nov. 8, 2018

Related U.S. Application Data

(63) Continuation-in-part of application No. PCT/CA2016/000291, filed on Nov. 23, 2016.
(Continued)

(51) Int. Cl.
*A61B 5/00* (2006.01)
*A61B 5/107* (2006.01)
(Continued)

(52) U.S. Cl.
CPC .......... *A61B 5/1075* (2013.01); *A61B 5/0002* (2013.01); *A61B 5/1071* (2013.01); *A61B 5/1072* (2013.01); *A61B 5/1121* (2013.01); *A61B 5/4561* (2013.01); *A61B 5/72* (2013.01); *A61B 5/742* (2013.01); *A61B 5/7405* (2013.01);
(Continued)

(58) Field of Classification Search
CPC ... A61B 5/1071; A61B 5/1072; A61B 5/1075; A61B 5/0002; A61B 5/1121
See application file for complete search history.

(56) References Cited

U.S. PATENT DOCUMENTS

| 4,229,883 A | 10/1980 | Kobashi |
| 4,464,840 A * | 8/1984 | Newland .................. G01B 7/06 33/552 |

(Continued)

FOREIGN PATENT DOCUMENTS

| CN | 203560341 | 4/2014 |
| CN | 104921730 | 9/2015 |

OTHER PUBLICATIONS

WIPO, Canadian International Searching Authority, International Search Report dated Feb. 2, 2017, International Patent Application No. PCT/CA2016000291, 5 Pages.
(Continued)

*Primary Examiner* — Max F Hindenburg
(74) *Attorney, Agent, or Firm* — Baumgartner Patent Law; Marc Baumgartner

(57) ABSTRACT

A system for displaying and collecting biomechanical measurements is provided. The system comprises: an electronic caliper including a bar, two arms slidably mounted on the bar and extending normal therefrom, a display module, and an electronic system housed in the display module and comprising a light emitting diode string of lights, a nine-axis sensor, firmware, a wireless radio, and a power source connector for electronic communication with a power source; and a remote computing device, the wireless radio in communication with the remote computing device. The electronic caliper and method of use thereof is also provided.

18 Claims, 5 Drawing Sheets

Related U.S. Application Data

(60) Provisional application No. 62/260,390, filed on Nov. 27, 2015.

(51) Int. Cl.
  *A61B 5/11* (2006.01)
  *G01B 3/38* (2006.01)

(52) U.S. Cl.
  CPC .............. *A61B 5/7475* (2013.01); *G01B 3/38* (2013.01); *A61B 5/4571* (2013.01); *A61B 5/4576* (2013.01); *A61B 2562/0219* (2013.01)

(56) References Cited

U.S. PATENT DOCUMENTS

| | | | |
|---|---|---|---|
| 5,249,366 A | 10/1993 | Takahasi et al. | |
| 5,966,827 A | 10/1999 | Horvath et al. | |
| 6,565,519 B2 | 5/2003 | Benesh | |
| 6,694,636 B1 * | 2/2004 | Maher | A61B 5/04023 33/1 C |
| 7,131,952 B1 | 11/2006 | Dickholtz, Sr. et al. | |
| 7,225,057 B2 | 5/2007 | Froman et al. | |
| 8,915,868 B1 | 12/2014 | Anderson | |
| 2005/0115093 A1 | 6/2005 | Chi et al. | |
| 2007/0097789 A1 * | 5/2007 | Coffey | G01S 13/08 367/99 |
| 2008/0052942 A1 | 3/2008 | Kawatoko | |
| 2008/0177503 A1 | 7/2008 | Stockman | |
| 2011/0030470 A1 | 2/2011 | Kim et al. | |
| 2011/0138645 A1 * | 6/2011 | Zhang | G01B 7/13 33/784 |
| 2012/0203504 A1 * | 8/2012 | Jordil | G01B 3/205 702/162 |
| 2014/0031700 A1 * | 1/2014 | Ferrantelli | A61B 5/1072 600/476 |
| 2014/0190030 A1 | 7/2014 | Sano | |
| 2015/0158423 A1 | 1/2015 | Schwantner | |

OTHER PUBLICATIONS

WIPO, Canadian International Searching Authority, Written Opinion of the International Searching Authority dated Feb. 2, 2017, International Patent Application No. PCT/CA2016000291, 5 Pages.

* cited by examiner

ELECTRONIC CALIPER FOR ASSESSING PATIENT BIOMECHANICS

CROSS REFERENCE TO RELATED APPLICATIONS

This present invention is a Continuation-in-Part of International Application No. PCT/CA2016/000291, filed Nov. 23, 2016, which designated the U.S. and claims priority to U.S. Application Ser. No. 62/260,390, filed Nov. 27, 2015, all entitled ELECTRONIC CALIPER FOR ASSESSING PATIENT BIOMECHANICS which are hereby incorporated in their entirety including all tables, figures, and claims.

FIELD

The present technology relates to an electronic caliper for measuring imbalances in patient posture. More specifically, the technology is a digital electronic caliper that allows a practitioner to easily view and interpret the results and allow for direct data collection and analysis by a computing device.

BACKGROUND

A standard hip and shoulder caliper is used in medicine to determine the alignment of the shoulders and the hips. It is comprised of a bar with two arms that can slide along the bar and a graduated numeric display with an indicator ball. In use, the arms are positioned on the shoulders or the hips of the patient, and the indicator ball moves to a position relative to the degree of unleveling. The practitioner views the position of the indicator ball and records the degree of unleveling. If the results are to be stored electronically, they must be manually entered into a computing device. This device does not allow for each of a visual and digital signal to be provided. Further, it does not allow for a digital signal to be sent to a computing device for processing and storage.

The anatometer is a more complex version of the hip and shoulder caliper. It includes a digital display and can record data. It, however, is a very large and costly device with many unnecessary components. Further, a numeric display provides a higher degree of accuracy than in needed for the practitioner.

What is needed is a simple to use, hand held caliper for measuring tilt, yaw and roll of a patient's shoulders and/or pelvis. The display would preferably be easy to view with a relevant level of accuracy. It would be preferably if the data could be transferred directly to a computing device, therefore, the device would preferably include Blue Tooth or a WiFi radio. It alternatively could include a Universal Serial Bus (USB) port for downloading data. It would be advantageous if the practitioner could view the display and discuss the results with a patient during the assessment.

SUMMARY

The present technology is a simple to use, hand held electronic calliper for measuring tilt, yaw and roll of a patient's shoulders and/or pelvis. The display is easy to view with a relevant level of accuracy. The data are digital and can be transferred directly to a computing device as the device includes a wireless radio or USB port, while at the same time, providing a display to allow a practitioner to discuss results in real time with the patient.

In one embodiment an electronic caliper for taking biomechanical measurements is provided, the electronic caliper comprising a bar, two arms slidably mounted on the bar and extending normal therefrom, a display module, an electronic system housed in the display module and including a light emitting diode string of lights, a nine-axis sensor, firmware, a communicator, and a power source connector for electronic communication with a power source.

In the electronic caliper, the nine-axis sensor may include a three-axis accelerometer, a three-axis gyroscope and a three-axis compass.

In the electronic caliper, the electronic system may further comprise a touch detector, and an on and off switch.

In the electronic caliper, the electronic system may further comprise a discriminator.

In the electronic caliper, the electronic system may further comprise a beeper.

In the electronic caliper, the communicator may be a wireless radio.

In the electronic caliper, the power source connector may be a battery connector.

In the electronic caliper, the electronic system may further comprise a battery.

In another embodiment, a system for displaying and collecting biomechanical measurements is provided, the system comprising: an electronic caliper including a bar, two arms slidably mounted on the bar and extending normal therefrom, a display module, and an electronic system housed in the display module and comprising a light emitting diode string of lights, a nine-axis sensor, firmware, a wireless radio, and a power source connector for electronic communication with a power source; and a remote computing device, the wireless radio in communication with the remote computing device.

In the system, the nine-axis sensor may include a three-axis accelerometer, a three-axis gyroscope and a three-axis compass.

In the system, the electronic system may further comprise a discriminator.

In the system, the electronic system may further comprise an on and off switch.

In the system, the electronic system may further comprise a touch detector.

In the system, the power source connector may be a battery connector and the power source may be a battery, housed within the display module.

In the system, the electronic system may further comprise a beeper.

In the system, the remote computing device may include a memory for instructing a processor to process an at least one data set received from the electronic caliper.

In another embodiment, a method of assessing biomechanics of a patient is provided, the method comprising a user: selecting an electronic caliper, the electronic caliper comprising a bar, two arms slidably mounted on the bar and extending normal therefrom, a display module, an electronic system housed in the display module and including a light emitting diode string of lights, a nine-axis sensor, firmware, a communicator, and a power source connector for electronic communication with a power source; placing the electronic caliper on a patient; and viewing the light emitting diode string of lights.

The method may further comprise the electronic caliper sending an at least one digital datum to a computing device.

The method may further comprise the user instructing the computing device to analyze the at least one digital datum.

The method may comprise measuring a pitch angle, a roll angle and a yaw angle.

The method may include processing the pitch angle, the roll angle and the yaw angle to provide a patient posture profile.

FIGURES

DESCRIPTION

Definitions

Biomechanical angle—in the context of the present technology, a biomechanical angle is any angle defined by a longitudinal axis of a patient and two points on the body.

Tilt angle—in the context of the present technology, a tilt angle is any angle defined by the longitudinal axis and one point of the body on one side and another point of the body on the other side, for example, the tilt angle of the shoulders is the height of one shoulder relative to the other shoulder.

Roll angle—in the context of the present technology, a roll angle is any angle defined by the longitudinal axis and one point of the body on the front and another point of the body on the back, for example, height of a point on the chest relative to height of the same point on the back.

Yaw angle—in the context of the present technology, a yaw angle is any angle defined by the longitudinal axis and two points of the body on the front or the back, for example, the position of the front of one shoulder relative to the position of the front of the other shoulder. This can also be referred to as twist angle.

DETAILED DESCRIPTION

Figure 1:
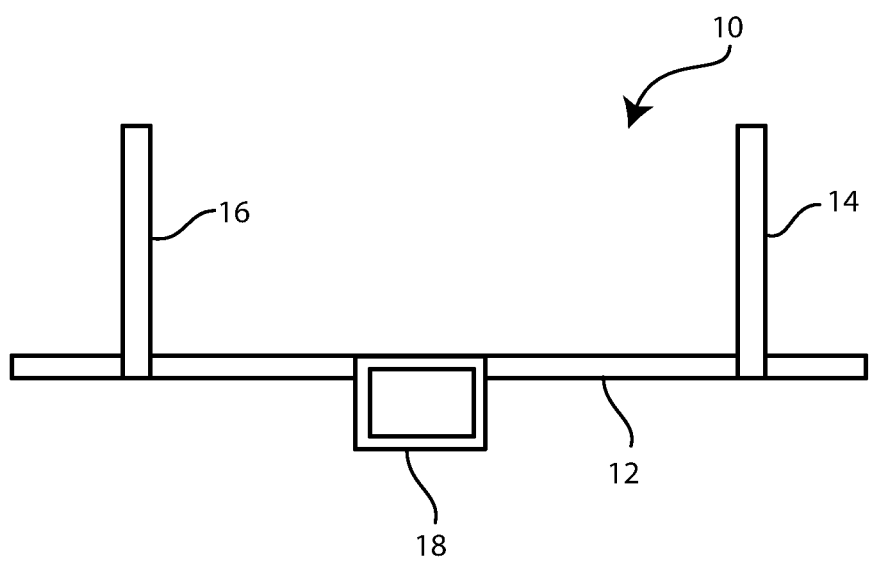
FIG. 1 is a front view of an electronic caliper of the present technology.
Figure 2:
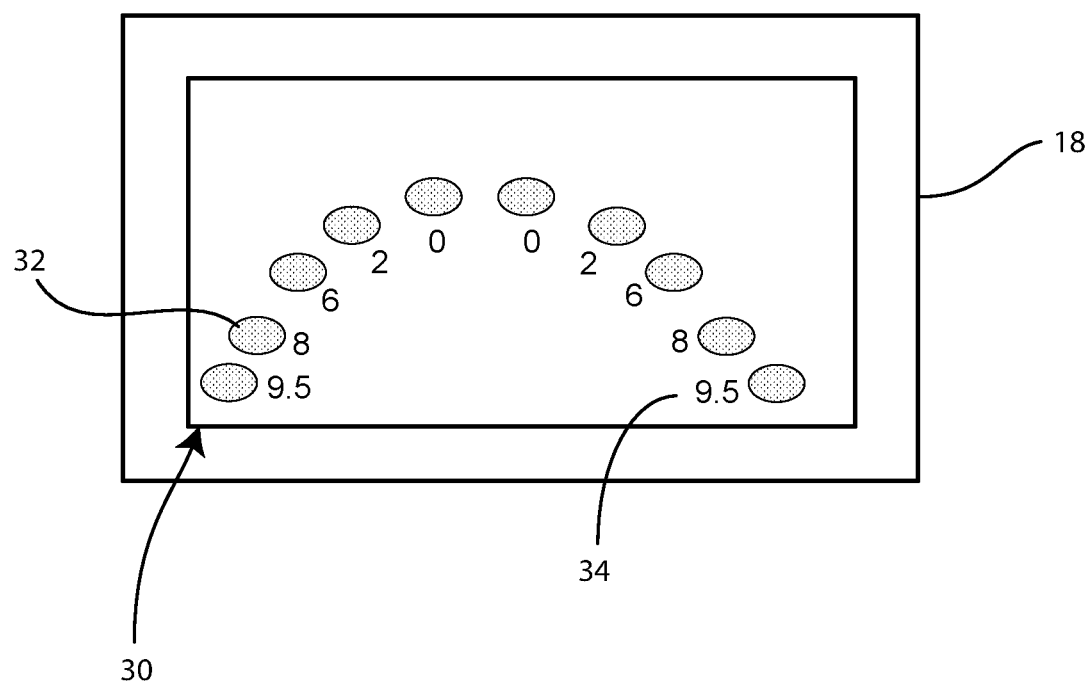
FIG. 2 is a front view of the display module of the caliper of FIG. 1.

As shown in FIG. 1, an electronic caliper, generally referred to as 10, has a bar 12, a first arm 14, a second arm 16 and a display module 18. The first and second arm 14, 16 are slidably mounted on the bar 12 to allow inward and outward adjustment. They extend outward from the bar at right angles to the bar. As shown in FIG. 2, the display module 18 includes a display, generally referred to as 30. The display 30 has a light emitting diode string of lights 32 and a scale 34.

Figure 3:
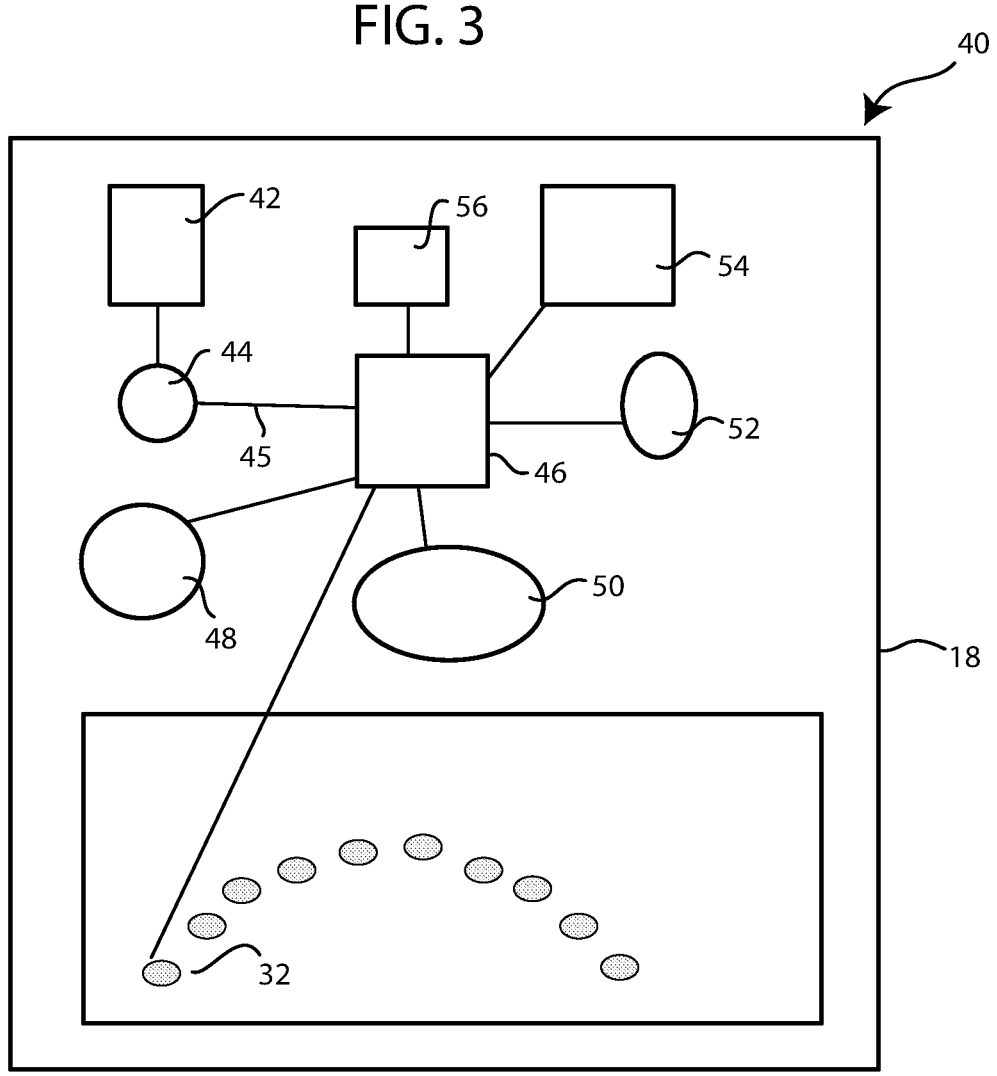
FIG. 3 is a plan view of the electronics of the caliper of FIG. 1.

The electronic system, generally referred to as 40 is shown in FIG. 3. It is housed in and is part of the display module 18. In the preferred embodiment, a touch detector 42 is in electronic communication with an on and off switch 44, which is in electronic communication, via a power source connector 45, with a battery 46. The battery 46 is in electronic communication with the light emitting diode string of lights 32, a beeper 48, a nine-axis motion tracking sensor 50 (which has a 3 axis gyroscope, a 3 axis accelerometer and a 3 axis digital compass), firmware 52, a data communicator 54, such as, but not limited to a wireless radio such as a Blue tooth radio and/or a universal serial bus, and a discriminator 56. The discriminator 56 is a circuit that includes a number of operational amplifiers.

Figure 4:
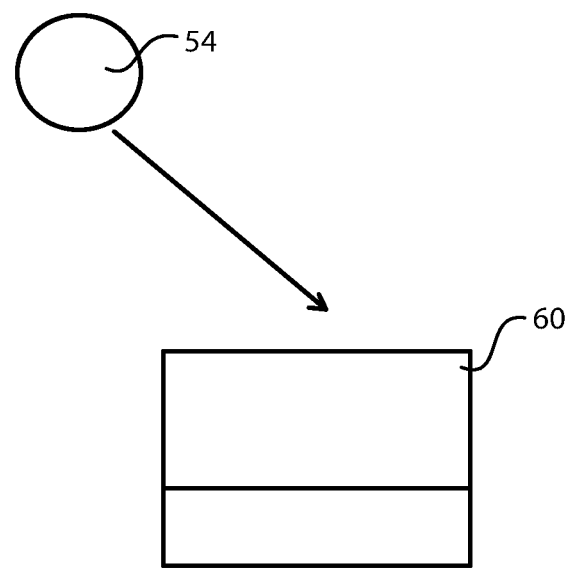
FIG. 4 is a front view of the system of the present technology.
Figure 5:
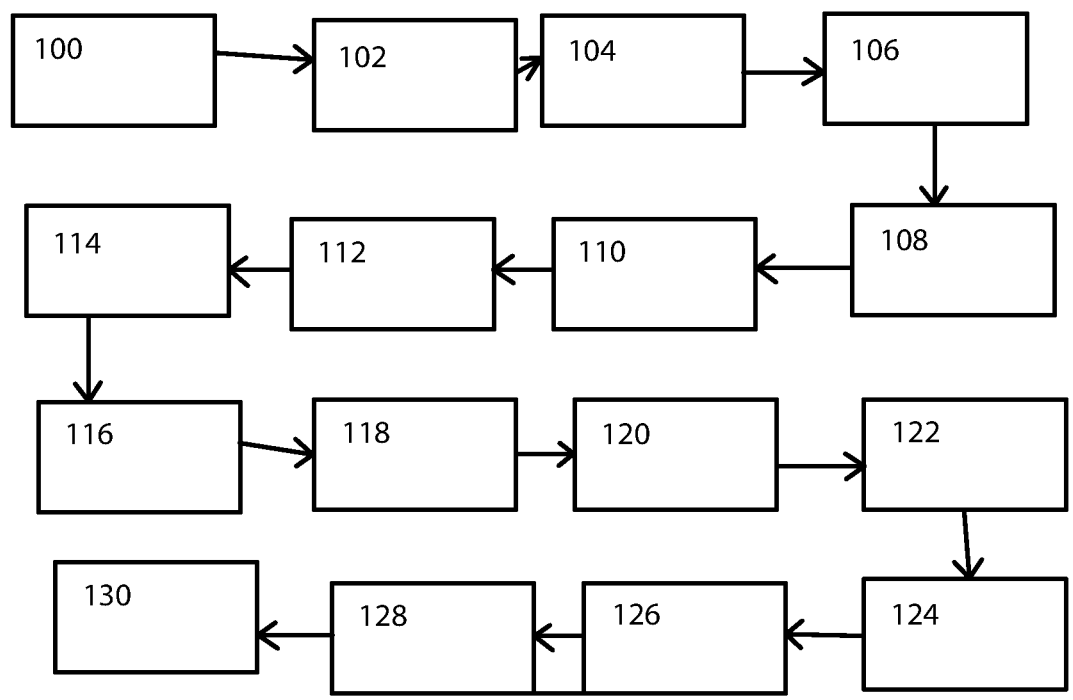
FIG. 5 is a block diagram outlining the typical steps taken in using the caliper of FIG. 1.

As shown in FIG. 4, the Blue tooth radio 54 communicates with a computing device 60. The computing device 60 includes a processor and a memory, the memory having instructions thereon for instructing the processor. Software in the memory allows for noise discrimination and provides calculations to transform the raw data into posture profiles for a given patient, or for a group of patients with the same or similar biomechanics. The posture profiles use data from each of the title angle, the roll angle and the yaw angle to provide a composite which is representative of the patient's posture. This can be further processed into change over time data.

In use, a user picks up 100 the electronic caliper 10, the touch detector 42 detects 102 contact and causes the on and off switch 44 to turn on 104 the electronic caliper 10. The user places 106 the electronic caliper 10 on the patient's hips or shoulders (note that the electronic calipers can also be used to measure other body parts, such as, but not limited to knees and ankles, however, these are not as significant as the shoulders and hips in terms of overall body alignment). The sensor 50 measures 108 the tilt angle of the patient's hips or shoulders. The sensor 50 continues 110 to measure the tilt angle until it is stable and the beeper 48 sounds 112 at that time. The discriminator 56 determines 114 whether the reading is a true reading or is false. The number of LED lights 32 in the string illuminate 116 proportional to the tilt angle. For example, if the tilt is 10 degrees, all the lights will be illuminated. If the tilt is 5 degrees, half of the lights will be illuminated. Rather than being a digital readout, that is far more accurate than is necessary, and hence subject to human error, the LED light string provides a suitable accuracy for the practitioner to view. This is about ½ degree increments from 0 to about 15 degrees or about 9.5 degrees and all degrees therebetween. The firmware 52 records 118 a digital output. This is highly accurate data. The digital output is sent 120 by the wireless radio 54 to the computing device 60. The computing device 60 then stores 122 the data. Further processing 124 of the data can occur, such as, but not limited to, graphing change over time, pooling data from patients having similar biomechanics, and determining trends in treatment outcomes. Once the shoulders or hips have been measured, the practitioner gently shakes 126 the electronic caliper 10, causing the sensor 50 to measure 128 a rapid change in direction, which in turn sends 130 a signal to the electronics 40 to reset. The process is repeated for whichever of the shoulders or hips that has not been measured.

A roll angle is also a concern for patient health. For this reason, the electronic caliper 10 can also be used to measure the roll angle of the hips and shoulders (note that the electronic calipers can also be used to measure other body parts, such as, but not limited to knees and ankles, however, these are not as significant as the shoulders and hips in terms of overall body alignment). In use, a user picks up the electronic caliper 10, the touch detector 42 detects contact and causes the on and off switch 44 to turn on the electronic caliper 10. The user places the electronic caliper 10 on the patient's hips or shoulders. The sensor 50 measures the roll angle of the patient's hips or shoulders. The sensor 50 continues to measure the roll angle until it is stable and the beeper 48 sounds at that time. The discriminator 56 determines whether the reading is a true reading or is false. The number of LED lights 32 in the string illuminate proportional to the roll angle. For example, if the roll is 10 degrees, all the lights will be illuminated. If the roll is 5 degrees, half of the lights will be illuminated. Rather than being a digital readout, that is far more accurate than is necessary, and hence subject to human error, the LED light string provides a suitable accuracy for the practitioner to view. This is about ½ degree increments from 0 to about 15 degrees or about 9.5 degrees and all degrees therebetween. The firmware 52 records a digital output. This is highly accurate data. The digital output is sent by the wireless radio 54 to the computing device 60. The computing device 60 then stores the data. Further processing of the data can occur, such as, but not limited to, graphing change over time, pooling data from patients having similar biomechanics, and determining trends in treatment outcomes. Once the shoulders or hips have been measured, the practitioner gently shakes the electronic caliper 10, causing the sensor 50 to measure a rapid change in direction, which in turn sends a signal to the electronics 40 to reset. The process is repeated for whichever of the shoulders or hips that has not been measured.

A yaw angle is also a concern for patient health. For this reason, the electronic caliper 10 can also be used to measure the yaw angle of the hips and shoulders (note that the electronic calipers can also be used to measure other body parts, such as, but not limited to knees and ankles, however, these are not as significant as the shoulders and hips in terms of overall body alignment). In use, a user picks up the electronic caliper 10, the touch detector 42 detects contact and causes the on and off switch 44 to turn on the electronic caliper 10. The user places the electronic caliper 10 on the patient's hips or shoulders. The sensor 50 measures the yaw angle of the patient's hips or shoulders. The sensor 50 continues to measure the roll angle until it is stable and the beeper 48 sounds at that time. The discriminator 56 determines whether the reading is a true reading or is false. The number of LED lights 32 in the string illuminate proportional to the yaw angle. For example, if the yaw is 10 degrees, all the lights will be illuminated. If the yaw is 5 degrees, half of the lights will be illuminated. Rather than being a digital readout, that is far more accurate than is necessary, and hence subject to human error, the LED light string provides a suitable accuracy for the practitioner to view. This is about ½ degree increments from 0 to about 15 degrees or about 9.5 degrees and all degrees therebetween. The firmware 52 records a digital output. This is highly accurate data. The digital output is sent by the wireless radio 54 to the computing device 60. The computing device 60 then stores the data. Further processing of the data can occur, such as, but not limited to, graphing change over time, pooling data from patients having similar biomechanics, and determining trends in treatment outcomes. Once the shoulders or hips have been measured, the practitioner gently shakes the electronic caliper 10, causing the sensor 50 to measure a rapid change in direction, which in turn sends a signal to the electronics 40 to reset. The process is repeated for whichever of the shoulders or hips that has not been measured.

Additional processing of the data can include compiling the tilt, roll and yaw data to obtain a profile of the patient's posture. Changes over time and in relation to treatment can be determined.

In an alternative embodiment, the electronic system may not include the touch detector, battery and on and off switch and may simply have a power source connector for connecting to an external power source. As would be known to one skilled in the art, this embodiment would be cumbersome as compared to the preferred embodiment.

The invention claimed is:

1. An electronic caliper for taking biomechanical measurements, the electronic caliper comprising a bar, two arms slidably mounted on the bar and extending normal therefrom, a display module, an electronic system housed in the display module and including a light emitting diode string of lights, a nine-axis sensor, firmware, a communicator, a touch detector, an on and off switch in electronic communication with the touch detector, and a power source connector for electronic communication with a power source.

2. The detector of claim 1, wherein the nine-axis sensor includes a three-axis accelerometer, a three-axis gyroscope and a three-axis compass.

3. The electronic caliper of claim 1, wherein the electronic system further comprises a discriminator.

4. The electronic caliper of claim 3, wherein the electronic system further comprises a beeper.

5. The electronic caliper of claim 4, wherein the communicator is a wireless radio.

6. The electronic caliper of claim 5, wherein the power source connector is a battery connector.

7. The electronic caliper of claim 6, wherein the electronic system further comprises a battery.

8. A system for displaying and collecting biomechanical measurements, the system comprising: an electronic caliper including a bar, two arms slidably mounted on the bar and extending normal therefrom, a display module, and an electronic system housed in the display module and comprising a light emitting diode string of lights, a nine-axis sensor, firmware, a wireless radio, a touch detector, an on and off switch in electronic communication with the touch detector, and a power source connector for electronic communication with a power source; and a remote computing device, the wireless radio in communication with the remote computing device.

9. The system of claim 8, wherein the nine-axis sensor includes a three-axis accelerometer, a three-axis gyroscope and a three-axis compass.

10. The system of claim 9, wherein the electronic system further comprises a discriminator.

11. The system of claim 10, wherein the power source connector is a battery connector and the power source is a battery, housed within the display module.

12. The system of claim 11, wherein the electronic system further comprises a beeper.

13. The system of claim 12, wherein the remote computing device includes a memory for instructing a processor to process an at least one data set received from the electronic caliper.

14. A method of assessing biomechanics of a patient, the method comprising a user: selecting an electronic caliper, the electronic caliper comprising a bar, two arms slidably mounted on the bar and extending normal therefrom, a display module, an electronic system housed in the display module and including a light emitting diode string of lights, a nine-axis sensor, firmware, a communicator, and a power source connector for electronic communication with a power source; placing the electronic caliper on a patient; viewing the light emitting diode string of lights; and the user resetting the electronic caliper by shaking the electronic caliper.

15. The method of claim 14, further comprising the electronic caliper sending an at least one digital datum to a computing device.

16. The method of claim 15, further comprising the user instructing the computing device to analyze the at least one digital datum.

17. The method of claim 16, wherein a pitch angle, a roll angle and a yaw angle are measured.

18. The method of claim 17, wherein the pitch angle, the roll angle and the yaw angle are processed to provide a patient posture profile.

* * * * *